(12) United States Patent
Lisogurski

(10) Patent No.: US 11,529,079 B2
(45) Date of Patent: Dec. 20, 2022

(54) REGIONAL SATURATION SYSTEM WITH ENSEMBLE AVERAGING

(71) Applicant: Covidien LP, Mansfield, MA (US)

(72) Inventor: Daniel Lisogurski, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 558 days.

(21) Appl. No.: 16/419,422

(22) Filed: May 22, 2019

(65) Prior Publication Data

US 2019/0269357 A1    Sep. 5, 2019

Related U.S. Application Data

(62) Division of application No. 15/067,769, filed on Mar. 11, 2016, now Pat. No. 10,342,466.

(60) Provisional application No. 62/137,314, filed on Mar. 24, 2015.

(51) Int. Cl.
  *A61B 5/1455* (2006.01)
  *A61B 5/00* (2006.01)

(52) U.S. Cl.
  CPC ...... *A61B 5/14551* (2013.01); *A61B 5/14553* (2013.01); *A61B 5/7203* (2013.01); *A61B 5/7278* (2013.01); *A61B 5/7285* (2013.01); *A61B 5/7289* (2013.01)

(58) Field of Classification Search
  None
  See application file for complete search history.

(56) References Cited

U.S. PATENT DOCUMENTS

| | | | |
|---|---|---|---|
| 4,960,126 A | 2/1990 | Conlon et al. | |
| 5,485,847 A | 1/1996 | Baker, Jr. | |
| 5,743,263 A | 4/1998 | Baker, Jr. | |
| 6,339,715 B1 | 1/2002 | Bahr et al. | |
| 6,516,209 B2 | 2/2003 | Cheng et al. | |
| 6,879,850 B2 | 4/2005 | Kimball | |
| 7,090,648 B2 | 8/2006 | Sackner et al. | |
| 7,194,293 B2 | 3/2007 | Baker, Jr. | |
| 7,209,774 B2 | 4/2007 | Baker, Jr. | |
| 7,225,013 B2 | 5/2007 | Geva et al. | |
| 7,392,075 B2 | 6/2008 | Baker, Jr. | |
| 7,534,212 B2 | 5/2009 | Baker, Jr. | |
| 8,108,022 B2 | 1/2012 | Balberg et al. | |

(Continued)

OTHER PUBLICATIONS

International Search Report and Written Opinion from International Application No. PCT/US2016/023598, dated Jun. 3, 2016, 12 pages.

(Continued)

*Primary Examiner* — Marjan Fardanesh
(74) *Attorney, Agent, or Firm* — Shumaker & Sieffert, P.A.

(57) ABSTRACT

A method may include receiving, at a processor, a first electromagnetic radiation signal and a second electromagnetic radiation signal from a regional oximetry sensor having two or more detectors and two or more emitters. The method may also include receiving, at the processor, a trigger signal that has a frequency corresponding to a periodic physical activity of a patient. Additionally, the method may include generating, via the processor, one or more ensemble averaged signals based at least in part on the first and second electromagnetic radiation signals and the trigger signal. Further, the method may include calculating, via the processor, a regional oxygen saturation value based at least in part on the one or more ensemble averaged signals and displaying, via a display, the regional oxygen saturation value.

20 Claims, 4 Drawing Sheets

(56) References Cited

U.S. PATENT DOCUMENTS

| 8,238,994 B2 | 8/2012 | Baker, Jr. |
| 8,401,608 B2 | 3/2013 | Baker, Jr. et al. |
| 8,588,878 B2 | 11/2013 | Li et al. |
| 10,342,466 B2 | 7/2019 | Lisogurski |
| 2005/0113656 A1 | 5/2005 | Chance |
| 2005/0197579 A1 | 9/2005 | Baker, Jr. |
| 2007/0100220 A1 | 5/2007 | Baker, Jr. |
| 2008/0076986 A1 | 3/2008 | Pav |
| 2008/0082009 A1 | 4/2008 | Baker |
| 2008/0262326 A1 | 10/2008 | Hete et al. |
| 2009/0326348 A1 | 12/2009 | Baker, Jr. |
| 2011/0041849 A1 | 2/2011 | Chen et al. |
| 2011/0112387 A1 | 5/2011 | Li et al. |
| 2011/0270048 A1 | 11/2011 | Addison et al. |
| 2012/0220844 A1 | 8/2012 | Baker, Jr. |
| 2014/0176944 A1 | 6/2014 | Addison et al. |
| 2014/0187883 A1 | 7/2014 | Lisogurski |
| 2014/0187884 A1 | 7/2014 | Addison et al. |
| 2014/0243632 A1 | 8/2014 | Ulrich et al. |

OTHER PUBLICATIONS

International Preliminary Report on Patentability from International Application No. PCT/US2016/023598, dated Sep. 26, 2017, 7 pages.

Prosecution History from U.S. Appl. No. 15/067,769, dated Aug. 6, 2018 through Feb. 21, 2019, 58 pages.

REGIONAL SATURATION SYSTEM WITH ENSEMBLE AVERAGING

CROSS-REFERENCE TO RELATED APPLICATION

This application is a divisional of U.S. patent application Ser. No. 15/067,769, entitled, "Regional Saturation System with Ensemble Averaging," and filed Mar. 11, 2016, which claims priority to and the benefit of U.S. Provisional Application No. 62/137,314, entitled "Regional Saturation System with Ensemble Averaging," filed Mar. 24, 2015, each of which is herein incorporated by reference in its entirety.

BACKGROUND

The present disclosure relates generally to regional oximetry and, more particularly, to ensemble averaging of pulses in a detected waveform from a regional oximeter.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical practitioners often desire to monitor certain physiological characteristics of their patients. Accordingly, a wide variety of devices have been developed for monitoring physiological characteristics. Such devices provide doctors and other healthcare personnel with the information they need to provide healthcare for their patients. As a result, such monitoring devices have become an indispensable part of modern medicine. One technique for monitoring certain physiological characteristics of a patient is commonly referred to as regional oximetry, and the devices built based upon regional oximetry techniques are commonly referred to as regional oximeters.

A regional oximeter is typically used to measure various physiological characteristics, such as the blood oxygen saturation within the venous, arterial, and capillary systems within a region of a patient. Measurement of these characteristics has been accomplished by use of a non-invasive sensor that passes light through a portion of a patient's blood perfused tissue and photo-electrically senses the absorption and scattering of light in such tissue. For example, a regional oximetry sensor may include one or more emitters that emit one or more wavelengths of light and two or more detectors that photo-electrically sense the absorption and/or scattering of the light after passage through a region of the patient's tissue. During operation, a regional oximeter typically compares the relative intensities of light received at the two or more detectors to determine a regional oxygen saturation ($rSO_2$) value that corresponds to the blood oxygen saturation within the venous, arterial, and capillary systems of the region of the patient's tissue.

Because the regional oximetry sensor detects light that has passed through the venous, arterial, and capillary systems of the region of the patient's tissue, the signal from the regional oximetry sensor (e.g., a photo-plethysmographic (PPG) signal) may include arterial pulses and venous pulses. Arterial pulses are caused by an increased volume of arterial blood ejected from the heart and may be used to determine arterial oxygen saturation. Venous pulses are caused by the return flow of venous blood to the heart and may be used to determine venous oxygen saturation. However, it may be difficult to identify the arterial and venous pulses in the PPG signal due to the placement of the regional oximetry sensor on the body (e.g., a location with a weak arterial pulse, such as the forehead) and the emitter-detector spacing of the regional oximetry sensor. Consequently, it may be difficult to separately determine arterial oxygen saturation and venous oxygen saturation using a regional oximetry sensor.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
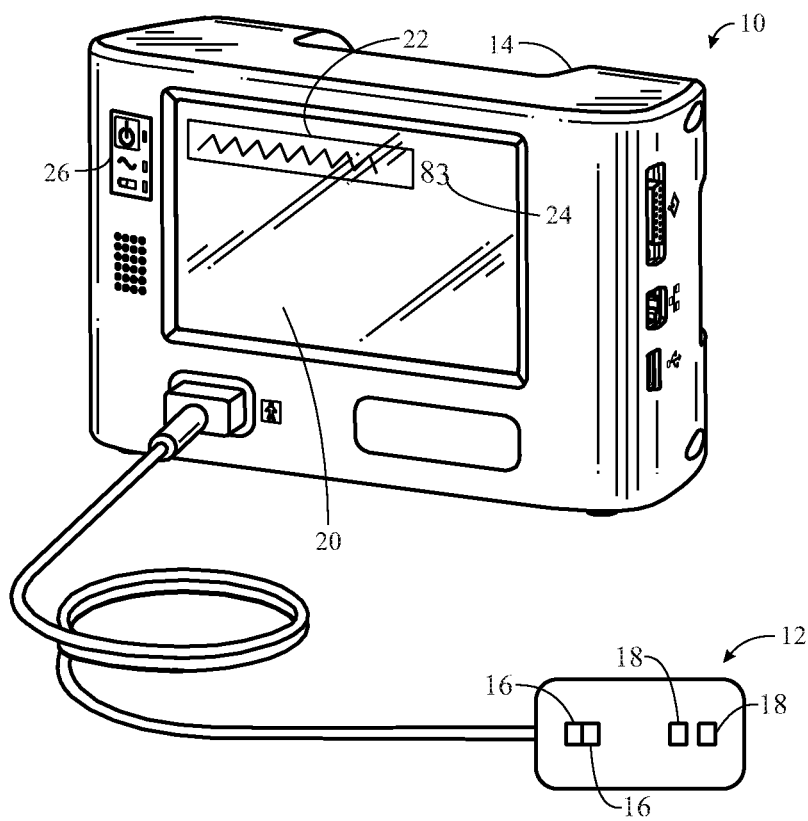
FIG. 1 is a perspective view of a medical system including a medical monitor and a regional oximetry sensor, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As noted above, the signal from a regional oximetry sensor (e.g., a photo-plethysmographic (PPG) signal) may include arterial pulses and venous pulses. Arterial pulses are related to the pulsatile flow of blood ejected from the heart, and as such, occur at a frequency corresponding to the cardiac cycle (e.g., heart rate) of a patient. Arterial pulses may be used to determine the patient's pulse rate and arterial oxygen saturation and may also be used to determine whether the sensor is on the patient. Periodic variations in venous blood volume (also called venous pulses in this document) are caused by the return flow of venous blood to the heart and may be used to determine venous oxygen saturation as well as to determine if the sensor is on the patient. The venous return varies from changing intrathoracic pressure during spontaneous respiration or mechanical ventilation, and as such, the venous pulses occur at a frequency corresponding to the respiration cycle of the patient. Accordingly, it may be desirable to extract the arterial pulses and venous pulses from the PPG signal to separately determine arterial oxygen saturation and venous oxygen saturation, as well as to determine whether the sensor is on the patient. However, it may be difficult to identify the arterial and/or venous pulses in the PPG signal from artifact pulses and noise because the PPG signal may have a low signal-to-noise ratio (e.g., due to the placement of the regional oximetry sensor on the body and/or the emitter-detector spacing of the regional oximetry sensor).

As described in detail below, the systems and methods provided herein are directed toward ensemble averaging pulses in a detected waveform from a regional oximeter based at least in part upon a trigger signal. Ensemble averaging is a temporal averaging scheme that may be utilized to combine similar signals or similar portions of the same signal in order to improve the SNR of the acquired data. In particular, ensemble averaging is used to calculate a weighted average of new samples and previous ensemble-averaged samples from one pulse-period earlier, and this weighted average may be utilized to determine a desired blood characteristic, such as arterial oxygen saturation and/or venous oxygen saturation or features extracted from the shape of an ensemble averaged arterial or venous cycle. For example, during a typical ensemble averaging operation, different weights may be assigned to different pulses, and a composite, averaged pulse waveform may be used to determine the desired blood characteristic.

The trigger signal, which will be described in more detail below, may be used to synchronize pulses of regional oximetry signals (e.g., arterial pulses or venous pulses) when computing an ensemble average. For example, the trigger signal may be a reference time or reference point used to determine or fix (e.g., define, identify, designate, establish, etc.) the temporal location of the pulse (e.g., the beginning and width of each pulse). Thus, rather than analyzing the regional oximetry signal to identify pulses, the trigger signal may be used to fix (e.g., define, identify, designate, establish, etc.) the temporal location of one or more pulses in the regional oximetry signal. Accordingly, during ensemble averaging, a number of pulses may be added together, with the beginning of each pulse or a relatively consistent offset from the start of each pulse determined by the trigger signal. In this manner, the pulses may add in phase and aperiodic portions of the signal (e.g., portions containing artifacts or physiological features which occur at a different rate than the trigger) that are not synchronized using the trigger signal may add in cancelling manner, which may increase the SNR of the detected pulses.

In certain embodiments, the trigger signal may have a frequency corresponding to a periodic activity of the patient. For example, in some embodiments, the trigger signal may have a frequency corresponding to a cardiac cycle of a patient and may be used to determine or define (e.g., identify, designate, establish, etc.) the location of arterial pulses in the PPG signal. In other embodiments, the trigger signal may have a frequency corresponding to a respiratory cycle of the patient and may be used to determine or define (e.g., identify, designate, establish, etc.) the location of venous pulses in the PPG signal. In some embodiments, the trigger may have a relatively consistent offset from the signal of interest which will result in a useful ensemble average with a corresponding phase shift. For example, a trigger from electrocardiography (ECG) R-wave detection or a pulse oximeter located on the periphery may be phase shifted relative to the timing of an arterial pulse collected from a regional saturation sensor located on the forehead. However, the trigger will occur at the correct rate and a simple time shift of the data corrects for the phase difference. For this reason, averaging may start slightly before the trigger and end slightly after the trigger.

With this in mind, FIG. 1 depicts an embodiment of a medical system 10 that may utilize a trigger signal to ensemble average one or more physiologic signals to determine one or more physiological characteristics of a patient. The medical system 10 includes a regional oximetry sensor 12 that is communicatively coupled to a medical monitor 14, which may be a regional oximetry monitor. The regional oximetry sensor 12 may be configured for use on a patient's head (e.g., forehead), back, stomach, heel, ear, arm, leg, or any other appropriate measurement site. Further, although only one regional oximetry sensor 12 is shown coupled to the medical monitor 14 in FIG. 1, in other embodiments, two, three, four, or more regional oximetry sensors 12 may be coupled to the medical monitor 14. For example, two regional oximetry sensors 12 may be used for cerebral oximetry and simultaneously two other regional oximetry sensors 12 used for somatic oximetry.

The regional oximetry sensor 12 may include two or more emitters 16 configured to emit light at two or more different wavelengths, such as light in the red and infrared range. The regional oximetry sensor 12 may also include two or more detectors 18: one that is relatively "close" to the two or more emitters 16 and one that is relatively "far" from the two or more emitters 16. The two or more detectors 18 detect the emitted light after it has passed through a region of the patient's tissue and generate photoplethysmography (PPG) signals based on the detected light. In one embodiment, the regional oximetry sensor 12 may include only one detector 18. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof.

The monitor 14 may include a processor configured to execute code (e.g., stored in a memory of the monitor 14 or received from another device) for filtering and/or processing the PPG signals from the regional oximetry sensor 12 to calculate physiological parameters, such as regional arterial oxygen saturation, regional venous oxygen saturation, regional mixed oxygen saturation, regional oxygen extraction ratio, and/or any other suitable physiological parameters. As will be described in more detail below, processing the PPG signals may include ensemble averaging the PPG signals using a trigger signal. For example, in one embodiment, the trigger signal may be determined by the monitor 14 using PPG signals from the "close" detector 18. That is, in some instances, the PPG signal detected by the "close" detector 18 may include arterial pulses that are sufficiently strong to be identified (e.g., detected) by the monitor 14, and the monitor 14 may be configured to use the detected arterial pulses from the "close" detector as a trigger signal to ensemble average PPG signals generated by the "far" detector. In other embodiments, the regional oximetry sensor 12 may include an even closer detector/emitter pair (e.g. 10 mm spacing) to generate a trigger and may use a different optical wavelengths in this emitter/detector pair such as, for example, a wavelength that has higher absorption in blood since the change in light levels will be greater with small changes in blood flow under the sensor. For example, in one embodiment, the regional oximetry sensor 12 may include an additional emitter 16 and/or an additional detector 18 (e.g., a third emitter 16 and/or a third detector 18) to create an emitter/detector pair with a spacing at or below a predetermined threshold (e.g., 10 mm), and this emitter/detector pair may be used for the trigger. Other embodiments with two sensors on the forehead (e.g., regional oximetry sensors 12) and two sensors on the body (e.g., regional oximetry sensors 12) may select the 'best' signal from all sensors to use as a trigger for all of them, or may combine the inputs from more than one sensor to generate a trigger by first averaging (or weighted averaging) of the signals collected from all emitter/detectors pairs.

Additionally, the processor of the monitor 14 may execute code (e.g., stored in a memory of the monitor 14 or received from another device) for filtering and/or processing the PPG signals from the regional oximetry sensor 12 to determine whether the regional oximetry sensor 12 is on the patient. As will be described in more detail below, the processor of the monitor 14 may determine one or more features of the PPG signals, such as the pulse amplitude, the pulse shape, the pulse period, the dicrotic notch, or any other suitable features, and may analyze the one or more features to determine whether the regional oximetry sensor 12 is on the patient. For example, the monitor 14 may analyze the one or more features of the PPG signals to determine whether the PPG signals include valid pulses (e.g., arterial pulses and/or venous pulses) and may determine that the regional oximetry sensor 16 is on the patient in response to a determination that the PPG signals include valid pulses. In some embodiments, the one or more features may not be visible or distinguishable in the raw PPG signals. As such, in some embodiments, processing the PPG signals may include ensemble averaging the PPG signals using a trigger signal. For example, by ensemble averaging the PPG signals using a trigger signal, the monitor 14 may determine or define (e.g., identify, designate, establish, etc.) the location of pulses (e.g., arterial pulses and/or venous pulses) in the PPG signal, and the monitor 14 may determine the one or more features from the pulses.

The monitor 14 also includes a display 20 configured to display information regarding the physiological parameters monitored by the regional oximetry sensor 12. For example, the display 20 may display one or more physiological waveforms 22, such as a PPG waveform, a regional arterial oxygen saturation waveform, a regional venous oxygen saturation waveform, a regional mixed oxygen saturation waveform, or any other suitable physiological waveforms. Additionally, the display 20 may display one or more calculated physiological parameters 24, such as regional arterial oxygen saturation, regional venous oxygen saturation, regional mixed oxygen saturation, regional oxygen extraction ratio, or any other suitable physiological parameter. The display 20 may also display information related to alarms, monitor settings, and/or signal quality. In certain embodiments, the display 20 may be a touch screen display. Additionally, the monitor 14 may include various control inputs 26, such as knobs, switches, keys and keypads, buttons, etc., for receiving user inputs.

Figure 2:
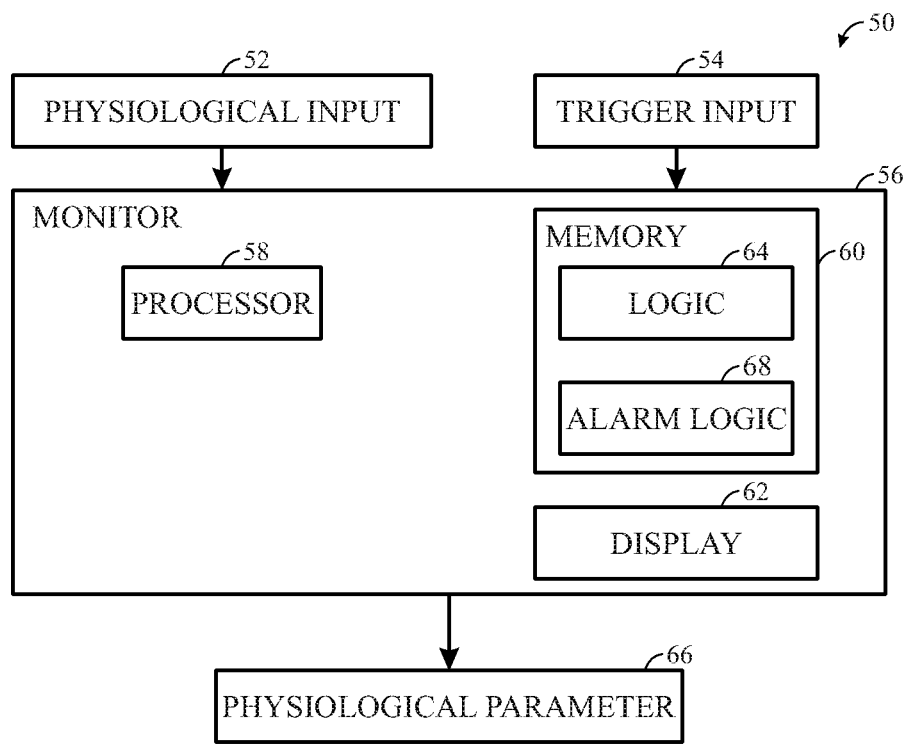
FIG. 2 is a block diagram of components of a medical system configured to receive a trigger input, in accordance with an embodiment.

FIG. 2 illustrates a block diagram of a processing system 50 for ensemble averaging a signal based on a trigger to determine a physiological parameter. The block diagram illustrates the interactions among some of the components of the system 50, including a physiological input 52, a trigger input 54, and a monitor 56 (e.g., the monitor 14). The monitor 56 includes a processor 58, a memory 60, and a display 62 (e.g., the display 20). The memory 60 may include instructions, code, and/or algorithms that may be read and executed by the processor 58 to perform the techniques disclosed herein. In certain embodiments, the physiological input 52 may include an incoming raw or processed physiologic signal. For example, in some embodiments, the physiological input 52 may be a filtered and/or amplified physiologic signal. In other embodiments, the physiological input 52 may include measured or calculated physiologic data. The physiological input 52 may be received from a sensor coupled to the patient (e.g., the regional oximetry sensor 12) or from other medical devices.

The trigger input 54 may include an incoming raw or processed signal, such as a raw or processed physiologic signal. The trigger input 54 may be received from a sensor coupled to the patient, a medical device, a processor-based device, and/or any suitable device. The trigger input 54 may be a signal with a frequency corresponding to a periodic physiological activity of a patient. For example, in certain embodiments, the trigger input 54 may be a signal with a frequency corresponding to a cardiac cycle of the patient. In other embodiments, the trigger input 54 may be a signal with a frequency corresponding to a respiratory cycle of the patient. Additionally, in some embodiments, the monitor 26 may be configured to receive a first trigger input 54 with a frequency corresponding to a cardiac cycle of the patient and a second trigger input 54 with a frequency corresponding to a respiratory cycle of the patient, and the first and second trigger inputs 54 may come from the same source or different sources. In other embodiments, the trigger input 54 may be a simulated physiologic signal with a frequency corresponding to a physiological activity of a patient. For example, the trigger input 54 may be a simulated physiological signal with a frequency corresponding to the patient's heart rate measured by a suitable medical monitor or a simulated physiological signal with a frequency corresponding to the patient's respiration rate measured by a suitable medical monitor.

In embodiments in which the trigger input 54 has a frequency corresponding to a cardiac cycle of the patient, the trigger input 54 may be received from a sensor, medical device, and/or processor-based device configured to monitor or determine information relating to the cardiac cycle of the patient, such as the heart rate of the patient or the electrocardiography (ECG) waveform of the patient. For example, the trigger input 54 may include a signal received from ECG electrodes configured to detect an ECG waveform of the patient or a signal received from an ECG monitor. In some embodiments, the trigger input 54 may be a signal received from a heart rate sensor or a heart rate monitor. In other embodiments, the trigger input 54 may include a signal received from a pulse oximetry sensor or a signal received from a pulse oximeter. Additionally, in other embodiments, the trigger input 54 may include a signal received from a blood pressure sensor, a blood pressure monitor, and/or a plethysmographic sensor. In certain embodiments, the pulse oximetry sensor providing the trigger input 54 may be attached to or integrated with the sensor providing the physiological input 52 (e.g., the regional oximetry sensor 12). In certain embodiments, the processor 58 may be configured to extract an arterial pulse waveform (e.g., a waveform including arterial pulses) from a PPG signal generated by a pulse oximetry sensor and to use the extracted arterial pulse waveform as the trigger input 54. A PPG signal generated by a pulse oximetry sensor may include stronger arterial pulses than a PPG signal generated by a regional oximetry sensor due to the placement of the pulse oximetry sensor compared to the placement of the regional oximetry sensor (e.g., a pulse oximetry sensor may be placed about a finger. which may have a strong arterial pulse, and a regional oximetry sensor may be placed about the forehead, which may have a weak arterial pulse). Additionally, a pulse oximetry sensor may be more sensitive to arterial pulses compared to regional oximetry sensors due to the closer emitter-detector spacing of the pulse oximetry sensor relative to the emitter-detector spacing of the regional oximetry sensor.

In certain embodiments, the trigger input 54 may be a signal received from the "close" detector 18 of the regional oximetry sensor 12. That is, in some instances, the signal generated by the "close" detector 18 may include sufficiently strong arterial pulses, which may be identified and/or extracted by the monitor 56. In some embodiments, the monitor 56 (e.g., the processor 58) may be configured to analyze a signal received from the "close" detector 18 to determine whether the signal includes identifiable arterial pulses (e.g., pulses having an amplitude above a predetermined threshold, pulses having a shape that corresponds to an arterial pulse, etc.). If the monitor 56 determines that the signal includes identifiable arterial pulses, the monitor 56 may determine that the regional oximetry sensor 16 is on the patient and may use the signal as the trigger input 54. If the monitor 56 determines that the signal from the "close" detector 18 does not include identifiable arterial pulses, the monitor 56 may be configured to utilize a trigger input 54 from a different source instead of the regional oximetry sensor 12. Other trigger sources that indicate the cardiac cycle may include blood pressure monitoring (e.g., via a blood pressure sensor) or artificial pacemakers.

In embodiments in which the trigger input 54 has a frequency corresponding to a respiratory cycle of the patient, the trigger input 54 may be received from a sensor, medical device, and/or processor-based device configured to monitor or determine information relating to the respiratory cycle of the patient, such as the respiration rate of the patient or the intrathoracic pressure of the patient. For example, the trigger input 54 may include a signal received from a capnograph, a ventilator, or a Zephyr™ patient monitor. In certain embodiments, the trigger input 54 may be a trans-thoracic impedance signal received from an ECG monitor, a nasal cannula or thermistor, a strain gauge on a respiration band, or a respiration impedance plethysmograph. In some embodiments, the trigger input 54 may be a signal from a pulse oximetry sensor or a pulse oximeter. For example, a pulse oximeter and/or the processor 58 may be configured to implement an algorithm to determine the patient's respiration rate from the PPG signal generated by a pulse oximetry sensor. In one embodiment, the processor 58 may receive a PPG signal from a pulse oximetry sensor, process the PPG signal to extract an arterial pulse waveform to generate a first trigger input 54 with a first frequency corresponding to a cardiac cycle of the patient, and process the PPG signal using a respiration rate algorithm to determine a second trigger input 54 with a second frequency corresponding to a respiratory cycle of the patient.

In certain embodiments, the monitor 56 may be configured process or qualify the trigger input 54 to extract and/or identify a desired trigger waveform, such as an arterial trigger waveform including arterial trigger pulses or a venous trigger waveform including venous trigger pulses. For example, the monitor 56 may include one or more filters configured to remove arterial pulses. In one embodiment, the filter may be a low pass filter that passes frequencies that are lower than the heart rate. In some embodiments, the filter may be adaptive or selected from a bank of filters based on estimated heart rates or respiration rates, or based on the input frequency of cardiac cycle (e.g., heart rate) or respiratory cycle (e.g., respiration rate) trigger inputs 54. When more than one trigger is available, an algorithm may select the best source or combine multiple triggers to generate an improved estimate.

The processor 58 may be configured to ensemble average the physiological input 52 using the trigger input 54. In particular, the trigger input 54 may be used by the processor 58 to determine or define (e.g., fix, establish, identify, etc.) the occurrence and period (e.g., duration) of one or more pulses in the physiological input 52. For example, in embodiments in which the trigger input 54 has a frequency corresponding to a cardiac cycle of the patient, the processor 58 may be configured to determine or define (e.g., fix, establish, identify, etc.) the beginning and end of one or more arterial pulses in the physiological input 52 based on the trigger input 54 (e.g., based on the patient's heartbeat). Further, in embodiments in which the trigger input 54 has a frequency corresponding to the respiratory cycle of the patient, the processor 58 may be configured to determine or define (e.g., fix, establish, identify, etc.) the beginning and end of one or more venous pulses in the physiological input 52 based on the trigger input 54 (e.g., based on the patient's respiration rate).

The processor 58 may then ensemble average the physiological input 52 by adding pulses of the physiological input 52 determined by the trigger input 54 so that the pulses add in phase and aperiodic portions of the physiological input 52 that are not synchronized using the trigger input 54 add in a cancelling manner to increase the SNR of the physiological input 52. For example, the processor 58 may add each new pulse of the physiological input 52 to a previous ensemble-averaged pulse from one pulse period earlier (e.g., the first pulse of the physiological input 52 may be used as the first ensemble-averaged pulse) to generate an updated ensemble-averaged physiological input 52 (e.g., an updated ensemble-averaged pulse of the physiological input 52). In some embodiments, the processor 58 may be configured to assign a weight to each pulse and combine the weighted pulses to generate the ensemble average. For example, in one embodiment, the new ensemble averaged pulse ($P_e$(new)) may be given by the following equation:

$$P_{e(new)[n]} = [(1-w_a) \times P_{e[n]}] + (w_a \times P_{p[k]}); \quad (1)$$

where $w_a$ is the assigned weight taking on a value between 0 and 1, $P_p$ is the most recent pulse, and $P_e$ is the current ensemble averaged pulse. However, any of a variety of weighted or non-weighted ensemble averaging methods known to those skilled in the art may be employed to combine pulses of the physiological input 52. In certain embodiments, the assigned weight, $w_a$, may be constant. In other embodiments, the assigned weight may be variable. Further, it should be noted that the weight may vary along the pulse. For example, if the peak and foot of the most recent pulse and ensemble averaged pulse substantially line up, a large portion of the most recent pulse may be used for averaging, but if the dicrotic notch appears out of alignment, less of this part of the most recent pulse may be used for averaging. As an alternative to equation (1), when the system has enough memory to store a number of past pulses, it may average them with equal weight as opposed to putting more weight on recent pulses. Different methods are possible depending on how quickly the signal of interest is changing. For example, if saturation is changing rapidly, putting more weight on recent pulses may be preferred but for slowly changing saturations, an equal weight over a certain history may give an improved estimate. The algorithm may also change in response to the pulse or respiration rate. For example, averaging 30 pulses may cover a minute long period in a patient with bradycardia or 15 seconds in a patient with tachycardia or a neonate. Additionally, the weighting of each pulse may be determined by the estimated signal quality. For example, irregular or ectopic beats may be excluded or weighed less in the averaging process as may pulses that appear noisy as determined by their frequency content, morphology, similarity to previous pulses or comparison to alternate waveforms such as pulses from a second sensor.

In certain embodiments, the processor 58 may be configured to assign a higher weight to pulses that are determined to be valid pulses and a lower weight to pulses that are determined to include noise, artifacts, and/or irregular features. To determine whether a pulse is a valid pulse or is a pulse including noise, artifacts and/or irregular features, the processor 58 may determine one or more features of the pulse, such as the pulse amplitude, the pulse shape, the pulse period, the dicrotic notch, or any other suitable features. In certain embodiments, the one or more features may not be visible or distinguishable in the raw PPG signal. As such, ensemble averaging using the trigger signal may be desirable to extract (e.g., determine) the one or more features from the PPG signal. The one or more features of the pulse may be provided as an input to logic 64 stored on the memory 60 of the monitor 56 to determine whether the pulse is a valid pulse or is a pulse that includes noise, artifacts, and/or irregular features (e.g., an ectopic or irregular arterial pulse). The logic 64 may compare the one or more features against one or more predetermined thresholds, predetermined threshold ranges, and/or one or more predetermined pulse shapes. In certain embodiments, the logic 64 may include a neural network, fuzzy logic classifier, a Bayesian network, and/or a mathematical model for analyzing the one or more features to determine whether the one or more features likely correspond to a valid pulse or a pulse containing noise, artifact, and/or irregular features. Additionally, the logic 64 may be configured to analyze the one or more features of the pulse (e.g., an ensemble averaged pulse), such as the pulse amplitude, the pulse shape, the pulse period, the dicrotic notch, or any other suitable features, to determine whether the sensor that provided the physiological input 52 (e.g., the regional oximetry sensor 12) is on the patient. For example, in some embodiments, the logic 64 may be configured to determine that the sensor is on the patient if the logic 64 determines that the pulse is a valid pulse based at least in part on the one or more features. In certain embodiments, the processor 58 may be configured to generate a user-perceivable indication (e.g., via a speaker and/or the display 62) in response to a determination that the sensor is not on the patient.

In certain embodiments, the processor 58 may be configured to process the one or more pulses determined by the trigger input 54 to account for variations in the frequency of the periodic physical activity of the patient (e.g., the cardiac cycle or the respiratory cycle). For example, the cardiac cycle (e.g., the heart rate) of the patient may vary slightly due to respiratory sinus arrhythmia, in which the heart rate changes slightly during the inhalation and exhalation phases of respiration. Additionally, the patient's respiration rate may also change over time. The time-varying heart rate and respiration rate may result in pulses (e.g., arterial pulses and venous pulses, respectively) that have varying pulse periods (e.g., widths). However, ensemble averaging pulses with varying pulse periods may result in blurring of the ensemble average.

Accordingly, in some embodiments, the processor 58 may be configured to reduce the weighting of pulses that differ from the average or implement a variety of linear or non-linear scaling methods to dynamically scale, stretch, or warp the width of the ensemble averaged pulse, the most recent pulse, or both, such that when the ensemble averaged pulse and the most recent pulse are combined (e.g., ensemble averaged), time axis uniformity of the most recent pulse and the ensemble averaged pulse has been established. That is, the processor 58 may be configured to dynamically scale, stretch, or warp the width of the ensemble averaged pulse, the most recent pulse, or both, to generate a substantially uniform width (e.g., a substantially equal width) for the ensemble averaged pulse and the most recent pulse. The processor 58 may be configured to dynamically scale, stretch, or warp the width of the ensemble averaged pulse, the most recent pulse, or both, using the methods discussed in U.S. Patent Publication No. 2014/0187884 and U.S. Patent Publication No. 2014/0187883, each of which are incorporated by reference in their entirety for all purposes. For example, in one embodiment, the processor 58 may be configured to identify one or more fiducial points (e.g., peaks, troughs, and so forth) of a waveform (e.g., the most recent pulse or the ensemble averaged pulse) and may dynamically scale, stretch, or warp the portions of the waveform between the one or more identified fiducial points. Additionally, in certain embodiments, the processor 58 may be configured to normalize or scale the vertical axis of the ensemble averaged pulse, the most recent pulse, or both.

The processor 58 may be configured to determine one or more physiological parameters 66 based at least in part upon the ensemble averaged pulses. In some embodiments, the processor 58 may be configured to determine or identify pulse rate and/or respiration rate based at least in part upon the ensemble averaged pulses (e.g., arterial pulses and/or venous pulses) using a variety of algorithms or methods known to those of skill in the art. In certain embodiments, the processor 58 may be configured to determine regional arterial oxygen saturation based at least in part upon the ensemble averaged arterial pulses. Additionally or alternatively, the processor 58 may be configured to determine regional venous oxygen saturation based at least in part upon the ensemble averaged venous pulses. That is, in some embodiments, the processor 58 may determine ensemble averages for both arterial pulses and venous pulses from the physiological input 52 to separately determine regional arterial oxygen saturation and regional venous oxygen saturation. Determining and displaying both regional arterial oxygen saturation and regional venous oxygen saturation, in addition to or instead of the regional mixed oxygen saturation, may be desirable because it may provide more information to the caregiver than only displaying the regional mixed oxygen saturation. For example, if the patient vasoconstricts or vasodilates or if the blood pressures changes, then the mix of arterial and venous blood assumed by typical regional saturation systems could be in error, so monitoring and displaying the venous oxygen saturation independently may be beneficial to provide additional information to the caregiver.

The processor 58 may be configured to determine the regional arterial oxygen saturation and the regional venous oxygen saturation from the arterial pulses and the venous pulses, respectively, using any of a variety of algorithms and methods known to those of skill in the art. For example, in some embodiments, the processor 58 may be configured to contrast the pulses for the two wavelengths (e.g., red and infrared) at each location (e.g., the "far" detector 18 and the "close" detector 18) to determine a regional saturation value that pertains to additional tissue through which the light received at the "far" detector 18 passed (tissue in addition to the tissue through which the light received by the "close" detector 18 passed, e.g., the brain tissue), when it was transmitted through a region of a patient (e.g., a patient's cranium). For example, the processor 58 may subtract the arterial pulses from the "close" detector 18 (e.g., the "shallow" pulses) from the arterial pulses from the "far" detector 18 (e.g., the "deep" pulses) for each wavelength to generate an arterial difference signal for each wavelength and may determine the regional arterial oxygen saturation based on the arterial difference signal for each wavelength. Similarly, the processor 58 may subtract the venous pulses from the "close" detector 18 (e.g., the "shallow" pulses) from the venous pulses from the "far" detector 18 (e.g., the "deep" pulses) for each wavelength to generate a venous difference signal for each wavelength and may determine the regional venous oxygen saturation based on the venous difference signal for each wavelength. In other embodiments, the processor 58 may be configured to subtract the PPG signal from the "close" detector 18 (e.g., the "shallow" PPG signal) from the PPG signal from the "far" detector (e.g., the "deep" PPG signal) for each wavelength to generate a difference signal for each wavelength before the PPG signals are ensemble averaged using the trigger input 54. In such embodiments, the difference signal for each wavelength may be ensemble averaged using the trigger input 54 to determine or define the arterial pulses or venous pulses.

In certain embodiments, the processor 58 may perform a ratio of ratios calculation based on the difference signal for each wavelength. For example, the processor 58 may calculate a first percent modulation for a first difference signal at a first wavelength of light by dividing the change in light level due to arterial pulses (sometimes called AC component) by the baseline (low frequency, sometimes called DC) component. Low frequency changes in the baseline due to respiration and other sources may be attenuated by high pass filtering or band pass filtering the light signal to isolate the arterial pulse frequency from the respiration. The processor 58 may similarly calculate a second percent modulation for a second difference signal at a second wavelength of light. The processor 58 may divide (e.g., take the ratio of) the first percent modulation at the first wavelength by the second percent modulation at the second wavelength to determine a ratio of ratios (e.g., an arterial ratio of ratios) which can be calibrated to a regional arterial oxygen saturation for specific wavelengths of light. For example, the processor 58 may determine the regional arterial oxygen saturation based on the ratio of ratios using a look-up table that correlates ratio of ratios values with regional arterial oxygen saturation. Similarly, the processor 58 may determine regional venous oxygen saturation by calculating a first percent modulation for a first difference signal at a first wavelength of light by dividing the change in light level due to venous pulses by the baseline. Arterial pulses may be attenuated by high pass filtering or band pass filtering. Additionally, the processor 58 may similarly calculate a second percent modulation for a second difference signal at a second wavelength of light and may divide the first percent modulation by the second percent modulation to determine the ratio of ratios (e.g., a venous ratio of ratios) which can be calibrated to a regional venous oxygen saturation for specific wavelengths of light. Accordingly, the processor 58 may determine the regional venous oxygen saturation based on the ratio of ratios using a look-up table that correlates ratio of ratios values with regional venous oxygen saturation.

In some embodiments, the processor 58 may be configured to determine a physiological parameter of the patient, such as regional arterial oxygen saturation, regional venous oxygen saturation, regional mixed oxygen saturation, pulse rate, or respiration rate, based at least in part upon one or more features extracted from the ensemble averaged pulse (e.g., venous pulses or arterial pulses). For example, the processor 58 may be configured to determine the physiological parameter based at least in part upon one or more features such as, but not limited to, the pulse amplitude, the pulse shape, the pulse period, and/or the dicrotic notch. It should be noted that in certain embodiments, these features may not be visible or distinguishable in the raw PPG signal. Thus, ensemble averaging the pulses using the trigger signal may be desirable to extract or determine the one or more features.

Additionally, in some embodiments, the processor 58 may be configured to determine a regional mixed oxygen saturation value based at least in part upon the regional arterial oxygen saturation and the regional venous oxygen saturation. For example, in one embodiment, the regional mixed oxygen saturation ($S_{r,m}O_2$) may be given by the following equation:

$$S_{r,m}O_2 = x(S_{r,a}O_2) + (1-x)(S_{r,v}O_2); \qquad (2)$$

where x is the percentage of regional blood volume that is arterial, $S_{r,a}O_2$ is the regional arterial oxygen saturation, and $S_{r,v}$ is the regional venous oxygen saturation. In certain embodiments, the value of x may be stored in the memory 60 of the monitor 56. In some embodiments, the value of x may be between approximately 15 percent and 40 percent, 20 percent and 30 percent, or any other suitable range. In one embodiment, the processor 58 may be configured to determine the value of x or modify a stored value of x based at least in part upon information from the physiological input 52, the arterial pulses, the venous pulses, or any combination thereof.

Further, in some embodiments, the processor 58 may be configured to determine an oxygen extraction ratio for the region of the tissue monitored by the sensor (e.g., the regional oximetry sensor 12) to generate the physiological input 52. The oxygen extraction ratio is the ratio of oxygen consumption to oxygen delivery and may provide additional information to a caregiver regarding the patient's condition. In one embodiment, the oxygen extraction ration ($O_2ER$) may be given by the following equation:

$$O_2ER = \frac{S_{r,a}O_2 - S_{r,v}O_2}{S_{r,a}O_2}; \quad (3)$$

where $S_{r,a}O_2$ is the regional arterial oxygen saturation and $S_{r,v}$ is the regional venous oxygen saturation.

The processor 58 may be configured to cause the display of the one or more physiological parameters 66 (e.g., the regional arterial oxygen saturation, the regional venous arterial oxygen saturation, the regional mixed oxygen saturation, the oxygen extraction ratio, and/or any other suitable physiological parameters) on the display 62. Additionally, the processor 58 may be configured to apply alarm logic 68 (e.g., stored on memory 60) that generates an alarm status for the one or more physiological parameters 66 based at least in part upon one or more alarm conditions stored in the memory 60. The processor 58 may activate an alarm by activating a sound, a buzzer, a vibration, a light, a text message, and so forth in response to a generated alarm status.

Figure 3:
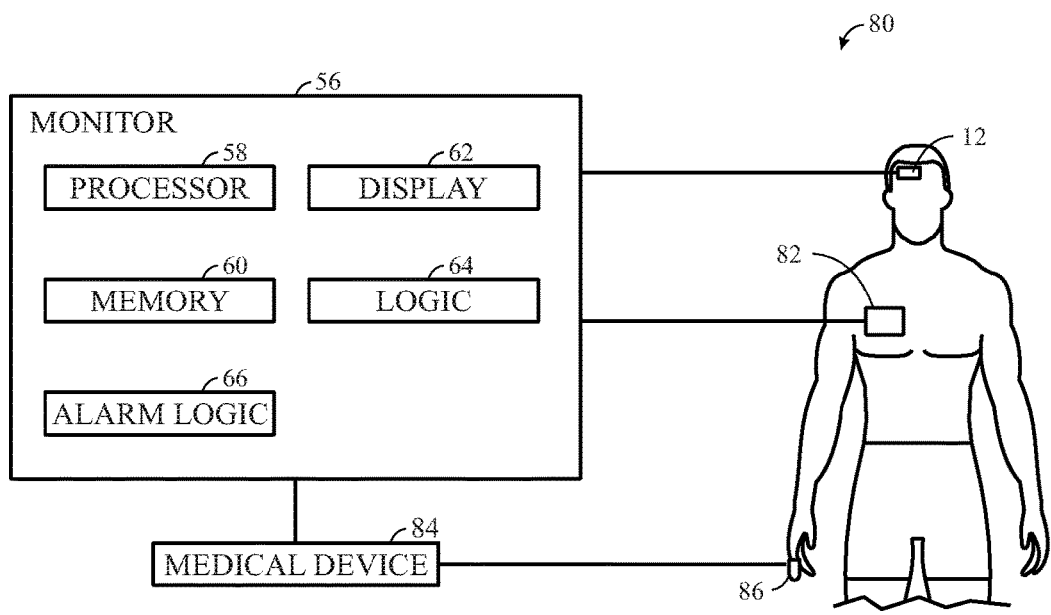
FIG. 3 is a schematic view of a medical system including a regional oximetry monitor configured to receive a trigger input from one or more external medical devices, in accordance with an embodiment.

As noted above, the monitor 56 may receive the trigger input 54 from a variety of sources that may be external to the monitor 56. For example, FIG. 3 illustrates an embodiment of a system 80 including the monitor 56 and the regional oximetry sensor 12, which is configured to provide the physiological input 52 to the monitor 56. As noted above, the regional oximetry sensor 12 may be configured to provide the trigger input 54 to the monitor 56 if the "close" detector 18 is able to detect a sufficiently strong arterial pulse. The processor 58 may analyze the signal from the "close" detector 18 to determine whether arterial pulses may be identified from the signal and used as the trigger input 54. If the processor 58 determines that the signal from the "close" detector 18 does not include identifiable or adequate arterial pulses to be used as the trigger input 54, the processor 58 may be configured to utilize a trigger input 54 received from a source external to the monitor 56.

For example, in certain embodiments, the monitor 56 may be communicatively coupled to one or more additional sensors 82 monitoring the patient. The one or more additional sensors 82 may be any suitable sensor configured to provide a signal having a frequency related to a periodic physical activity of the patient, a signal having a frequency related to a cardiac cycle of the patient, a signal having a frequency related to a respiratory cycle of the patient, or any combination thereof. For example, the one or more additional sensors 82 may include, but are not limited to, an ECG sensor, a pulse oximetry sensor, a heart rate sensor, a blood pressure sensor, a plethsymographic sensor, a thermistor (e.g., in or on a nasal cannula), and/or a strain gauge (e.g., on a respiration band). It should be appreciated that the monitor 56 may be configured to process (e.g., filter, amplify, etc.) signals received from the one or more additional sensors 82 to generate a suitable trigger input 54. For example, in one embodiment, the monitor 56 may be configured to remove pulsatile portions (e.g., via a low pass filter) of a signal having a frequency related to a respiratory cycle of the patient. In one embodiment, the monitor 56 may be configured to analyze signals received from two or more additional sensors 82 and may select the signal with the highest signal quality to use as the trigger input 54. In other embodiments, the monitor 56 may combine signals two or more additional sensors 82 to generate the trigger input 54.

Additionally or alternatively, the monitor 56 may be communicatively coupled to one or more medical devices 84 monitoring the patient and/or providing therapeutic treatments to the patient. The one or more medical devices 84 may be any suitable medical device configured to provide a signal having a frequency related to a periodic physical activity of the patient, a signal having a frequency related to a cardiac cycle of the patient, a signal having a frequency related to a respiratory cycle of the patient, or any combination thereof. For example, the one or more medical devices 84 may include, but are not limited to, a pulse oximeter, an ECG monitor, a capnograph, a ventilator, a blood pressure monitor, or a Zephyr™ patient monitor, or any combination thereof. It should be appreciated that, in certain embodiments, the one or more medical devices 84 may be configured to receive signals from one or more sensors 86 monitoring the patient, and the one or more medical devices 84 may be configured to process the signals received from the one or more sensors 86 to generate the a signal having a frequency related to a periodic physical activity of the patient, a signal having a frequency related to a cardiac cycle of the patient, a signal having a frequency related to a respiratory cycle of the patient, or any combination thereof. Further, it should be noted that in some embodiments, the monitor 56 may be configured to process (e.g., filter, amplify, etc.) signals received from the one or more medical devices 84 to generate a suitable trigger input 54.

Figure 4:
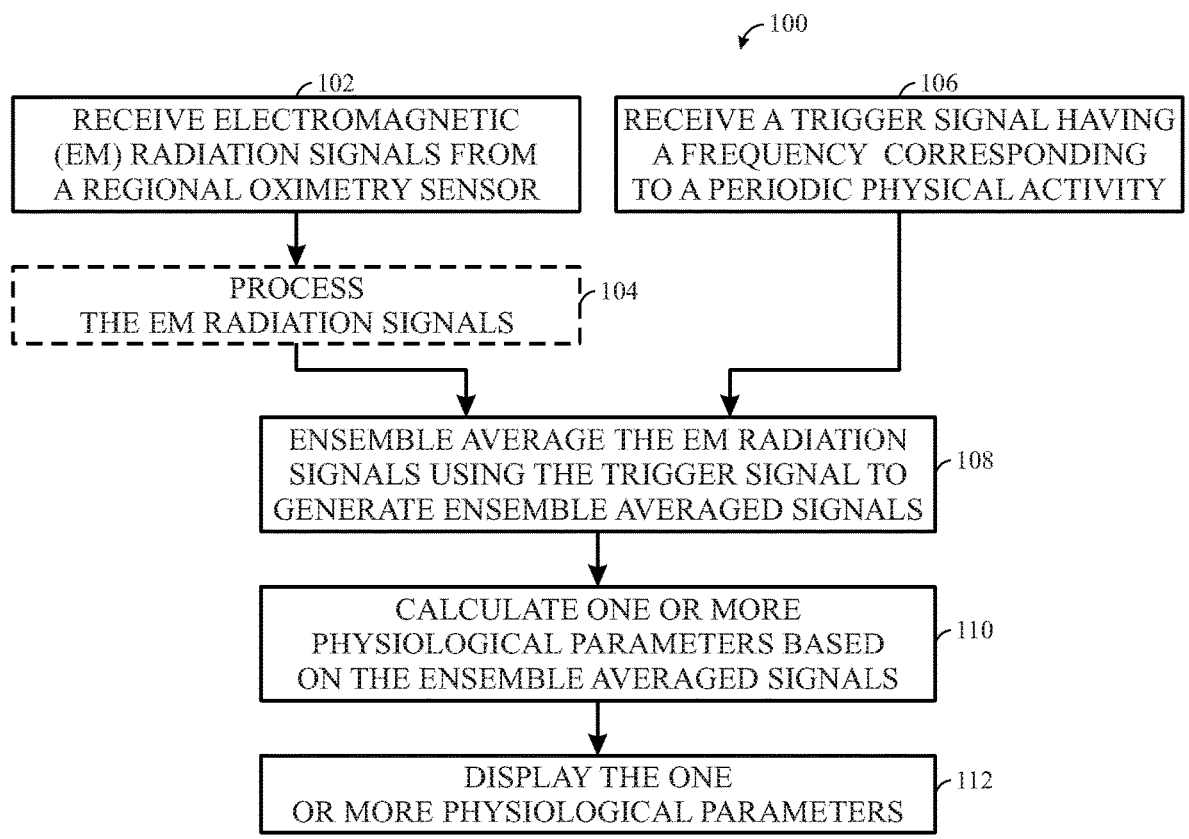
FIG. 4 illustrates a flow diagram of a method for calculating physiological parameters based at least in part on a trigger signal having a frequency corresponding to a periodic physical activity of a patient, in accordance with an embodiment.

The present embodiments also provide various methods for ensemble averaging signals based at least in part on a trigger input and determining physiological parameters based on the ensemble averaged signals. For example, FIG. 4 illustrates a method 100 for calculating physiological parameters based at least in part on a trigger signal having a frequency corresponding to a periodic physical activity of a patient. The method 100 includes receiving (e.g., via the monitor 56) electromagnetic (EM) radiation signals from a regional oximetry sensor (e.g., the regional oximetry sensor 12) monitoring a patient (block 102). In certain embodiments, the monitor 56 may receive a first EM signal from the "close" detector 18 of the regional oximetry sensor 12 and a second EM signal from the "far" detector 18 of the regional oximetry sensor 12. Additionally, in some embodiments, both of the first and second EM signals may be generated in response to returned light emitted from the emitters 16 that are configured to emit two wavelengths of light (e.g., red and infrared). The method 100 may optionally include processing (e.g., via the monitor 56) the received EM signals (block 104). Processing the received EM signals may include filtering the EM signals to remove certain frequencies and/or amplifying the EM signals. In some embodiments, processing the received EM signals may include subtracting the first EM signal from the "close" detector 18 from the second EM signal from the "far" detector 18. Additionally, the method 100 includes receiving (e.g., via the monitor 56) a trigger signal (e.g., the trigger input 54) having a frequency corresponding to a periodic physical activity of the patient (block 106). For example, the trigger signal may have a frequency corresponding to a cardiac cycle of the patient or a frequency corresponding to a respiratory cycle of the patient. The trigger signal may be received from any of the sources described in detail above.

The method 100 also includes ensemble averaging (e.g., via the processor 58) the received EM signals using the received trigger signal to generate one or more ensemble averaged signals (block 108). For example, in certain embodiments, the regional oximetry sensor 12 may be configured to emit two wavelengths of light (e.g., red and infrared), and the processor 58 may be configured to separately ensemble average a first signal corresponding to the first wavelength of light and a second signal corresponding to the second wavelength of light. Further, in certain embodiments, the processor 58 may be configured to separately ensemble average the signals received from the "far" detector 18 of the regional oximetry sensor 12 and the signals received from the "close" detector 18 of the regional oximetry sensor 12. Accordingly, in some embodiments, the processor 58 may generate a first ensemble averaged signal corresponding to the first wavelength of light from the "far" detector 18, a second ensemble averaged signal corresponding to the first wavelength of light from the "close" detector 18, a third ensemble averaged signal corresponding to the second wavelength of light from the "far" detector 18, and a fourth ensemble averaged signal corresponding to the second wavelength of light from the "close" detector 18. The processor 58 may subtract the ensemble averaged signal for the "close" detector 18 from the ensemble averaged signal from the "far" detector 18 for each wavelength. For example, the processor 58 may subtract the second ensemble averaged signal from the first ensemble averaged signal and may subtract the fourth ensemble averaged signal from the third ensemble averaged signal. In other embodiments, the processor 58 may subtract the EM signals from the "close" detector 18 from the EM signals from the "far" detector 18 before the EM signals are ensemble averaged, and the processor 58 may ensemble average the difference EM signal. The processor 58 may be configured to ensemble average the received EM signals using the trigger signal to determine or define (e.g., establish, identify, etc.) one or more pulses (e.g., arterial pulses or venous pulses) in the EM signals, as described in detail above.

Additionally, the method 100 includes calculating (e.g., via the processor 58) one or more physiological parameters (e.g., the one or more physiological parameters 66) based at least in part on the one or more ensemble averaged signals (block 110). The processor 58 may be configured to implement any of suitable algorithm and/or method, such as the algorithms and techniques described in detail above to, to calculate one or more desired physiological parameters. For example, as described above, the processor 58 may be configured to calculate regional arterial oxygen saturation, regional venous oxygen saturation, regional mixed oxygen saturation, and/or a regional oxygen extraction ratio. Further, the method 100 includes displaying (e.g., via the display 62) the one or more physiological parameters (block 112).

Figure 5:
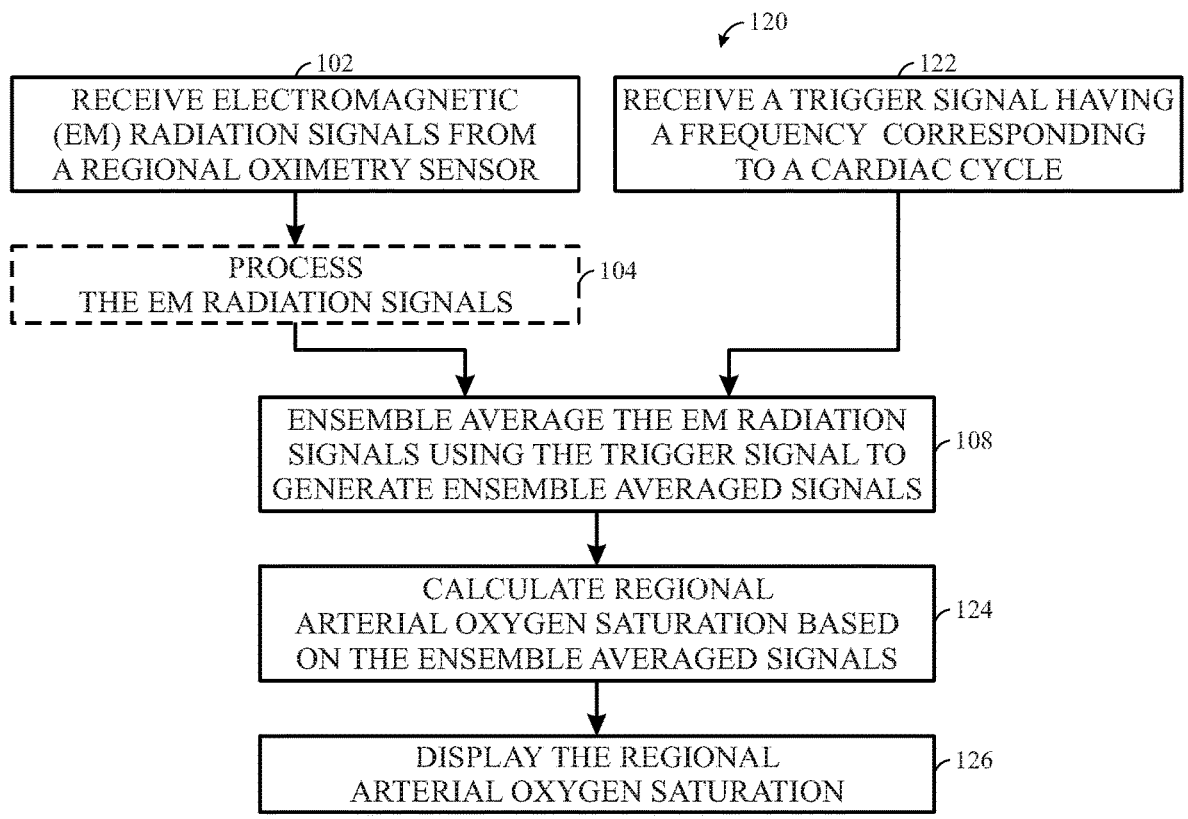
FIG. 5 illustrates a flow diagram of a method for calculating regional arterial oxygen saturation based at least in part on a trigger signal having a frequency corresponding to a cardiac cycle of a patient, in accordance with an embodiment.

FIG. 5 illustrates a method 120 calculating regional arterial oxygen saturation based at least in part on a trigger signal having a frequency corresponding to a cardiac cycle of a patient. The method 120 includes receiving (e.g., via the monitor 56) electromagnetic (EM) radiation signals from a regional oximetry sensor (e.g., the regional oximetry sensor 12) monitoring a patient (block 102) and, optionally, includes processing (e.g., via the monitor 56) the received EM signals (block 104), as described above in FIG. 4. The method 120 also includes receiving (e.g., via the monitor 56) a trigger signal having a frequency corresponding to a cardiac cycle of the patient (block 122). The trigger signal may be received from any suitable sources, such as a pulse oximetry sensor, a pulse oximeter, an ECG sensor, an ECG monitor, and/or a heart rate monitor.

Additionally, the method 120 includes ensemble averaging (e.g., via the processor 58) the received EM signals using the received trigger signal to generate one or more ensemble averaged signals (block 108), as described in FIG. 4. As noted above in FIG. 2, ensemble averaging EM signals based on a trigger with a frequency corresponding to a cardiac signal of the patient may enable the processor 58 to ensemble average arterial pulses of the EM signals, and the arterial pulses may be used to determine regional arterial oxygen saturation. Accordingly, the method 120 includes calculating (e.g., via the processor 58) regional arterial oxygen saturation based on the one or more ensemble averaged signals (block 124) and displaying (e.g., via the display 62) the regional arterial oxygen saturation (block 126).

Figure 6:
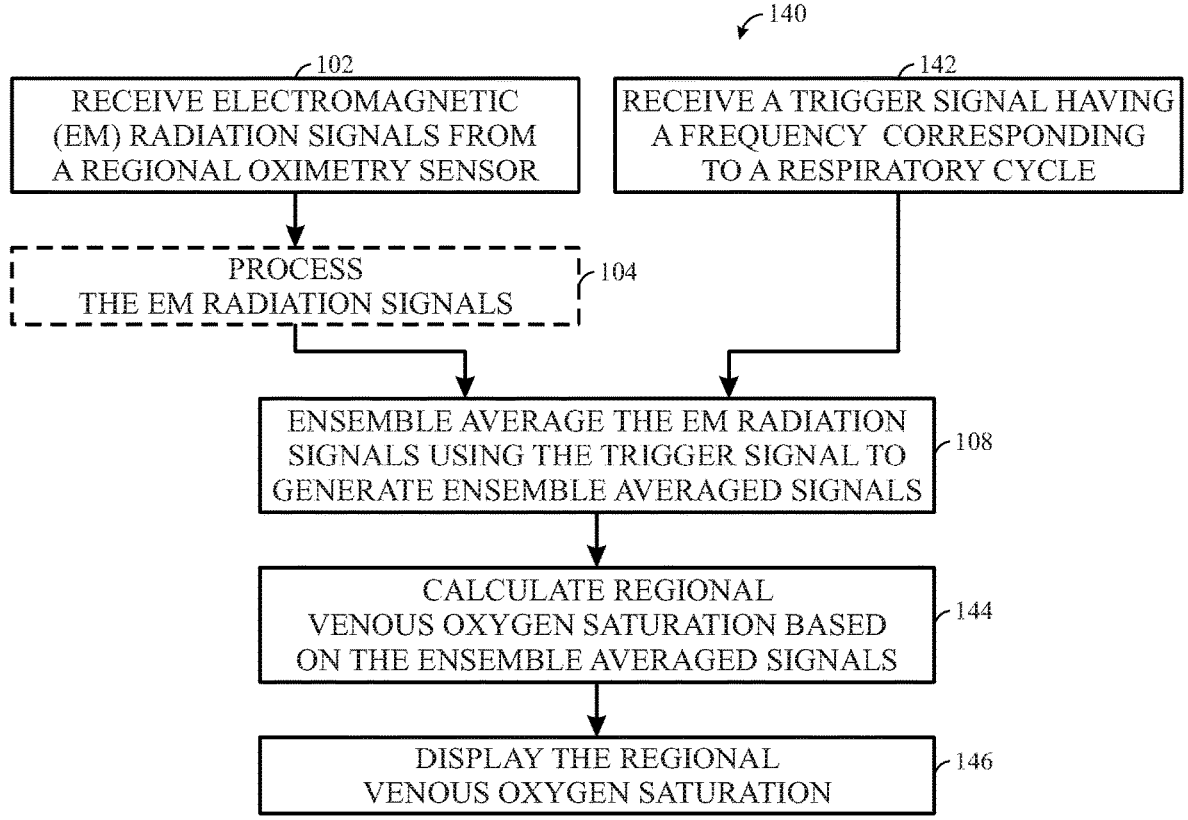
FIG. 6 illustrates a flow diagram of a method for calculating regional venous oxygen saturation based at least in part on a trigger signal having a frequency corresponding to a respiratory cycle of a patient, in accordance with an embodiment.

FIG. 6 illustrates a method 140 calculating regional venous oxygen saturation based at least in part on a trigger signal having a frequency corresponding to a respiratory cycle of a patient. The method 140 includes receiving (e.g., via the monitor 56) electromagnetic (EM) radiation signals from a regional oximetry sensor (e.g., the regional oximetry sensor 12) monitoring a patient (block 102) and, optionally, includes processing (e.g., via the monitor 56) the received EM signals (block 104), as described above in FIG. 4. The method 140 also includes receiving (e.g., via the monitor 56) a trigger signal having a frequency corresponding to a respiratory cycle of the patient (block 142). The trigger signal may be received from any suitable sources, such as a pulse oximeter (e.g., a pulse oximeter configured to determine the patient's heart rate from a PPG signal), a capnograph, a ventilator, or a Zephyr™ patient monitor, an ECG monitor, a strain gauge (e.g., on a respiration band), and/or a thermistor (e.g., in a nasal cannula).

Additionally, the method 140 includes ensemble averaging (e.g., via the processor 58) the received EM signals using the received trigger signal to generate one or more ensemble averaged signals (block 108), as described in FIG. 4. As noted above in FIG. 2, ensemble averaging EM signals based on a trigger with a frequency corresponding to a respiratory signal of the patient may enable the processor 58 to ensemble average venous pulses of the EM signals, and the venous pulses may be used to determine regional venous oxygen saturation. Accordingly, the method 140 includes calculating (e.g., via the processor 58) regional venous oxygen saturation based on the one or more ensemble averaged signals (block 144) and displaying (e.g., via the display 62) the regional venous oxygen saturation (block 146).

Figure 7:
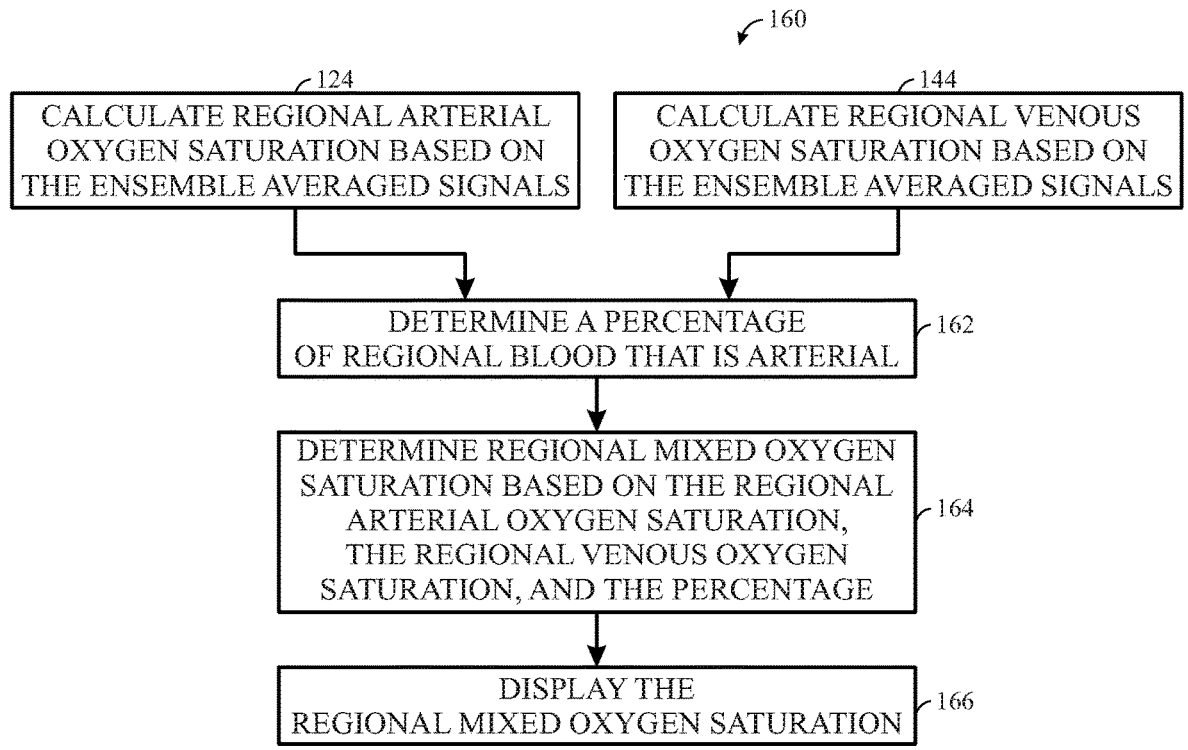
FIG. 7 illustrates a flow diagram of a method for calculating regional mixed saturation based at least in part on a regional arterial oxygen saturation value and a regional venous oxygen saturation value, in accordance with an embodiment.

Further, FIG. 7 illustrates a method 160 for calculating regional mixed saturation based at least in part on a regional arterial oxygen saturation value and a regional venous oxygen saturation value. The method 160 includes calculating regional arterial oxygen saturation (block 124), as described above in FIG. 5, and calculating regional venous oxygen saturation (block 144), as described above in FIG. 6. The method 160 also includes determining (e.g., via the processor 58) a percentage of regional blood volume that is arterial (block 162). Determining the percentage of arterial blood may include retrieving the percentage from the memory 60 of the monitor 56. In some embodiments, determining the percentage of arterial blood may include determining the percentage or modifying a stored percentage based at least in part upon information from the received EM signals (e.g., the arterial pulses and/or the venous pulses of the received EM signals). Additionally, the method 160 includes determining (e.g., via the processor 58) regional mixed oxygen saturation based at least in part on the regional arterial oxygen saturation, the regional venous oxygen saturation, and the percentage of arterial regional blood (block 164). In certain embodiments, the processor 58 may determining the regional mixed oxygen saturation using Equation 2, as described above in FIG. 2. Further, the method 160 includes displaying (e.g., via the display 62) the regional mixed oxygen saturation (block 166). In certain embodiments, the method 160 may also include displaying (e.g., via the display 62) the regional arterial oxygen saturation and/or the regional venous oxygen saturation.

Figure 8:
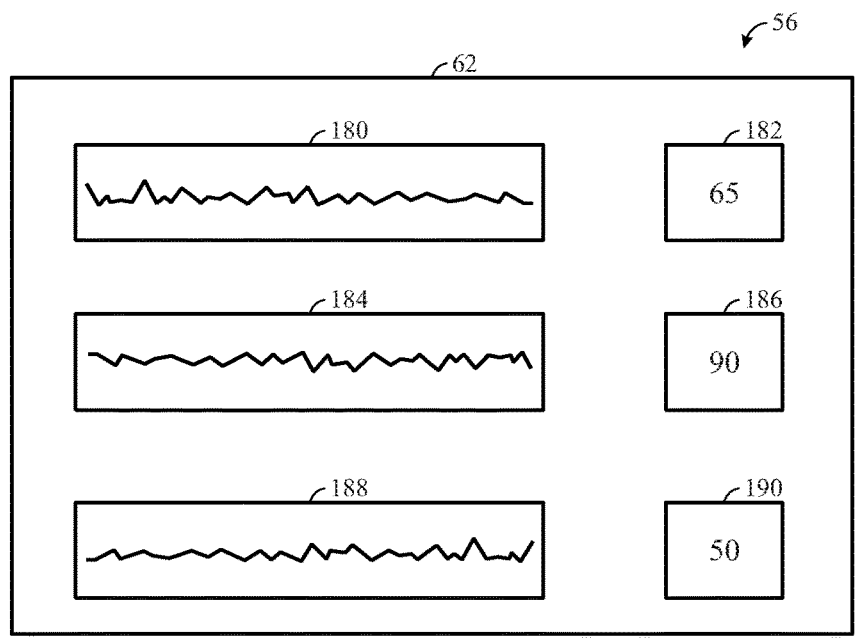
FIG. 8 is a perspective view of a medical monitor displaying regional arterial oxygen saturation, regional venous oxygen saturation, and regional mixed oxygen saturation.

As described in detail above, the systems and methods disclosed herein provide techniques for determining and displaying regional arterial oxygen saturation, the regional venous oxygen saturation, and regional mixed oxygen saturation. FIG. 8 illustrates an embodiment of the display 62 of the monitor 56 displaying information relating to regional arterial oxygen saturation, the regional venous oxygen saturation, and regional arterial oxygen saturation and/or the regional venous oxygen saturation. In particular, the display 62 may display a regional mixed oxygen saturation waveform 180 and a regional mixed oxygen saturation value 182 (e.g., a real-time value). Further, the display 62 may display a regional arterial oxygen saturation waveform 184 and a regional arterial oxygen saturation value 186. Additionally, the display 62 may display a regional venous oxygen saturation waveform 188 and a regional arterial oxygen saturation value 190.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A system, comprising:
a regional oximetry sensor comprising two or more emitters and two or more detectors, wherein the regional oximetry sensor is configured to generate a first electromagnetic radiation signal and a second electromagnetic radiation signal, wherein a first detector of the two or more detectors is spaced apart from the two or more emitters at a first distance and a second detector of the two or more detectors is spaced apart from the two or more emitters at a second distance that is greater than the first distance, wherein the first electromagnetic radiation signal is generated by the first detector of the two or more detectors and the second electromagnetic radiation signal is generated by the second detector of the two or more detectors, and wherein the first electromagnetic radiation signal and the second electromagnetic radiation signal each comprises arterial pulses and venous pulses; and
a patient monitor comprising a processor configured to:
receive the first and second electromagnetic radiation signals from the regional oximetry sensor;
receive a trigger signal that has a frequency corresponding to a periodic physical activity of a patient, wherein the trigger signal is determined from the first electromagnetic radiation signal;
generate one or more ensemble averaged signals based at least in part on the first and second electromagnetic radiation signals and the trigger signal;
determine the regional oximetry sensor is not disposed on the patient based at least in part on one or more features of the one or more ensemble averaged signals; and
generate a user-perceivable indication in response to a determination that the regional oximetry sensor is not disposed on the patient.

2. The system of claim 1, wherein the one or more features of the one or more ensemble averaged signals comprise a pulse amplitude, a pulse shape, a pulse period, a dicrotic notch, or any combination thereof.

3. The system of claim 1, wherein the processor is configured to determine the regional oximetry sensor is not disposed on the patient based at least in part on the one or more features of the one or more ensemble averaged signals by at least:
determining whether the one or more ensemble averaged signals include one or more arterial pulses based on the one or more features; and
determining that the regional oximetry sensor is not disposed on the patient in response to determining that the one or more ensemble averaged signals do not include one or more arterial pulses.

4. The system of claim 1, wherein the processor is configured to determine or define a location of one or more pulses in the one or more ensemble averaged signals based on the frequency of the trigger signal and determine the one or more features of the one or more ensemble averaged signals based on the location of the one or more pulses.

5. The system of claim 1, wherein the periodic physical activity includes a cardiac cycle of the patient.

6. The system of claim 1, wherein the periodic physical activity includes a respiratory cycle of the patient.

7. The system of claim 1, wherein the processor is configured to generate the one or more ensemble averaged signals by at least:
subtracting the first electromagnetic radiation signal from the second electromagnetic radiation signal to generate a difference electromagnetic radiation signal; and
ensemble averaging the difference electromagnetic radiation signal utilizing the trigger signal to generate the one or more ensemble averaged signals.

8. The system of claim 1, wherein the processor is configured to generate the one or more ensemble averaged signals by at least determining or defining a location of pulses in the one or more ensemble averaged signals based on the frequency of the trigger signal.

9. The system of claim 1, further comprising a medical device configured to generate the trigger signal, wherein the medical device comprises at least one of an electrocardiogram sensor, a pulse oximetry sensor, a heart rate sensor, a blood pressure sensor, a plethsymographic sensor, a thermistor, a strain gauge, a capnograph, a ventilator, or a blood pressure monitor.

10. The system of claim 1, wherein the processor is configured to determine the trigger signal based on the first electromagnetic radiation signal, the first electromagnetic radiation signal comprising a photoplethysmography (PPG) signal.

11. The system of claim 1, wherein the processor is configured to determine a regional oxygen saturation value based at least in part upon the one or more features of the one or more ensemble averaged signals.

12. A method, comprising:
receiving, by a processor, first and second electromagnetic radiation signals from a regional oximetry sensor, wherein the regional oximetry sensor includes two or more emitters and two or more detectors, wherein a first detector of the two or more detectors is spaced apart from the two or more emitters at a first distance and a second detector of the two or more detectors is spaced apart from the two or more emitters at a second distance that is greater than the first distance, wherein the first electromagnetic radiation signal is generated by the first detector of the two or more detectors and the second electromagnetic radiation signal is generated by the second detector of the two or more detectors, and wherein the first electromagnetic radiation signal and the second electromagnetic radiation signal each comprises arterial pulses and venous pulses;

receiving, by the processor, a trigger signal that has a frequency corresponding to a periodic physical activity of a patient, wherein the trigger signal is determined from the first electromagnetic radiation signal;

generating, by the processor, one or more ensemble averaged signals based at least in part on the first and second electromagnetic radiation signals and the trigger signal;

determining, by the processor, that the regional oximetry sensor is not disposed on the patient based at least in part on one or more features of the one or more ensemble averaged signals; and generating a user-perceivable indication in response to determining that the regional oximetry sensor is not disposed on the patient.

13. The method of claim 12, wherein the one or more features of the one or more ensemble averaged signals comprise a pulse amplitude, a pulse shape, a pulse period, a dicrotic notch, or any combination thereof.

14. The method of claim 12, wherein determining that the regional oximetry sensor is not disposed on the patient based at least in part on the one or more features of the one or more ensemble averaged signals comprises:

determining the one or more ensemble averaged signals do not include one or more arterial pulses based on the one or more features; and determining that the regional oximetry sensor is not disposed on the patient in response to determining that the one or more ensemble averaged signals do not include one or more arterial pulses.

15. The method of claim 12, further comprising:

determining or defining a location of one or more pulses in the one or more ensemble averaged signals based on the frequency of the trigger signal; and determining the one or more features of the one or more ensemble averaged signals based on the location of the one or more pulses.

16. The method of claim 12, wherein the periodic physical activity includes a cardiac cycle or a respiratory cycle of the patient.

17. The method of claim 12, generating the one or more ensemble averaged signals comprises:

subtracting the first electromagnetic radiation signal from the second electromagnetic radiation signal to generate a difference electromagnetic radiation signal; and ensemble averaging the difference electromagnetic radiation signal utilizing the trigger signal to generate the one or more ensemble averaged signals.

18. The method of claim 12, wherein generating the one or more ensemble averaged signals comprises determining or defining a location of pulses in the one or more ensemble averaged signals based on the frequency of the trigger signal.

19. The method of claim 12, wherein receiving the trigger signal comprises receiving the trigger signal from a medical device, wherein the medical device comprises at least one of an electrocardiogram sensor, a pulse oximetry sensor, a heart rate sensor, a blood pressure sensor, a plethsymographic sensor, a thermistor, a strain gauge, a capnograph, a ventilator, or a blood pressure monitor.

20. The method of claim 12, further comprising determining a regional oxygen saturation value based at least in part upon the one or more features of the one or more ensemble averaged signals.

* * * * *